(12) United States Patent
Natsch et al.

(10) Patent No.: US 9,440,097 B2
(45) Date of Patent: Sep. 13, 2016

(54) ORGANIC COMPOUNDS

(75) Inventors: Andreas Natsch, Uetikon (CH);
Michael Wasescha, Bassersdorf (CH)

(73) Assignee: Givaudan SA, Vernier (CH)

( * ) Notice: Subject to any disclaimer, the term of this patent is extended or adjusted under 35 U.S.C. 154(b) by 1409 days.

(21) Appl. No.: 13/006,791

(22) Filed: Jan. 14, 2011
(Under 37 CFR 1.47)

(65) Prior Publication Data
US 2012/0184513 A1 Jul. 19, 2012

Related U.S. Application Data

(62) Division of application No. 12/066,518, filed as application No. PCT/CH2006/000481 on Sep. 8, 2006, now abandoned.

(30) Foreign Application Priority Data

Sep. 12, 2005 (GB) .................................. 0518558.2

(51) Int. Cl.
| | | |
|---|---|---|
| A61K 8/33 | (2006.01) | |
| A61K 8/37 | (2006.01) | |
| A61K 8/40 | (2006.01) | |
| A61K 31/275 | (2006.01) | |
| A61Q 13/00 | (2006.01) | |
| A61Q 15/00 | (2006.01) | |
| A61Q 19/00 | (2006.01) | |

(52) U.S. Cl.
CPC ............... *A61Q 19/00* (2013.01); *A61K 8/33* (2013.01); *A61K 8/37* (2013.01); *A61K 8/40* (2013.01); *A61Q 13/00* (2013.01); *A61Q 15/00* (2013.01); *A61K 31/275* (2013.01); *A61K 2800/75* (2013.01)

(58) Field of Classification Search
CPC ............ A61K 8/33; A61K 8/37; A61K 8/40; A61K 2800/75; A61K 31/618; A61K 31/275; A61Q 13/00; A61Q 15/00; A61Q 19/00
See application file for complete search history.

(56) References Cited

U.S. PATENT DOCUMENTS

| | | | |
|---|---|---|---|
| 6,069,125 A | 5/2000 | Pesaro | |
| 6,727,221 B1 * | 4/2004 | Wilson et al. ................... | 512/1 |
| 2006/0003896 A1 | 1/2006 | Seo et al. | |

FOREIGN PATENT DOCUMENTS

| | | | |
|---|---|---|---|
| EP | 0545556 A2 | 6/1993 | |
| EP | 1552814 A1 | 7/2005 | |
| JP | 59170011 A | 9/1984 | |
| JP | 06271442 A * | 9/1994 | |
| WO | 8707842 A1 | 12/1987 | |
| WO | 9736252 A1 | 10/1997 | |
| WO | 9930720 A1 | 6/1999 | |

OTHER PUBLICATIONS

English language abstract of JP 5917011A found on Esp@cenet.com, 2001.
"New Cosmetic Science", edited by Takeo Mitsui, Nanzando, Jan. 18, 2001, pp. 132-134.
English language translation of relevant part of "New Cosmetic Science" edited by Takeo Mitsui, Nanzando, Jan. 18, 2001, pp. 132-134.

* cited by examiner

*Primary Examiner* — Sarah Pihonak
(74) *Attorney, Agent, or Firm* — Norris McLaughlin & Marcus PA

(57) ABSTRACT

The invention relates to organic compounds having the ability to reduce or suppress the onset of skin irritation induced by extraneous cause selected from the group of 2-heptylcyclopentanone, 2-ethoxynaphthalene; 2-methoxynaphthalene; 1-methoxy-4-(prop-1-enyl)benzene; 1-(cyclopropylmethyl)-4-methoxybenzene;

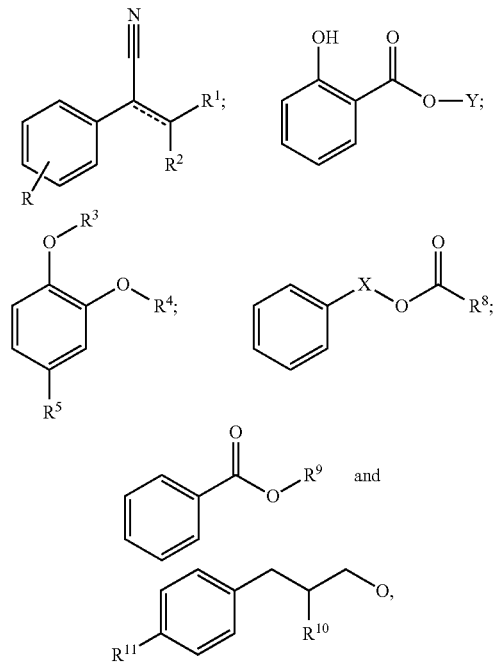

wherein X, Y, and $R^1$ to $R^{11}$ have the same meaning as given in the description.
Furthermore the invention refers to compositions for topical application to the skin comprising them. It further relates to a method of reducing or suppressing the formation of skin irritation.

4 Claims, No Drawings

ORGANIC COMPOUNDS

This is a Divisional patent application of copending patent application U.S. Ser. No. 12/066,518, which in turn is a patent application filed under 35 USC 371 of PCT/CH2006/000481.

The present invention relates to organic compounds having the ability to reduce or suppress the formation of skin irritation induced by extraneous causes, and to compositions comprising them for topical application to the skin. It further relates to a method of reducing or suppressing the onset of skin irritation by extraneous causes.

The human skin is constantly exposed to environmental stresses, such as heat and cold, air pollution, exceptionally dry air or exaggerated UV irradiation. A further form of stress can come from the application of cosmetic products or personal wash products.

For example, certain soap acids and some surfactants, in particular anionic and cationic surfactants, are known to stress the skin. Antiperspirant salts, such as aluminum salts and zirconium salts contained in antiperspirant products, retinol and derivatives thereof contained in anti-aging products, α-hydroxy acids such as glycolic acid or lactic acid contained in anti-wrinkle products are also known to stress the skin.

It is known from the art that prostaglandins are mediators being formed upon a wide variety of different forms of external stress applied to the human skin, which may become apparent in redness of the skin, particularly on normal, healthy skin. Thus there is a need for additives in topical application compositions, such as cosmetic products and personal wash products, which suppress or reduce the formation of prostaglandins, in particular prostaglandin $E_2$ ($PGE_2$).

Surprisingly the inventors have found that certain classes of chemical compounds, most of which are known as fragrance ingredients, have the ability to reduce or suppress the formation of prostaglandins in skin cells.

Thus the present invention refers in one aspect to the use of a compound for the preparation of topical skin care compositions for reduction of skin irritation, wherein the compound is selected from the list consisting of (a) compounds of the formula

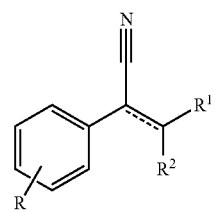

(a)

wherein

R is hydrogen or isopropyl;

$R^1$ is methyl or ethyl; and $R^2$ is $C_1$-$C_6$ alkyl or $C_2$-$C_6$ alkenyl; or $R^1$ and $R^2$ together with the carbon atom to which they are attached form a $C_5$ or $C_6$ cycloalkyl ring; and the dotted line together with the carbon carbon bond represents a single bond or a double bond;

(b) compounds of the formula

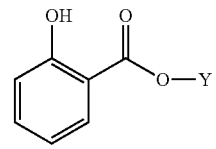

(b)

wherein Y is a $C_4$-$C_7$ hydrocarbon residue, e.g. cyclohexyl, n-hexyl, n-pentyl, iso-butyl, cis-3-hexen-1-yl, phenethyl, and 1-methyl-hex-3-en-1-yl;

(c) compounds of the formula

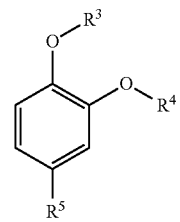

(c)

wherein $R^4$ is methyl or ethyl and

I) $R^3$ is hydrogen and $R^5$ is —$CH_2$—O—$R^6$, wherein $R^6$ is methyl or isopropyl; or II) $R^3$ is —C(O)—$R^7$, wherein $R^7$ is benzyl, and $R^5$ is —$CH_2$—CH=$CH_2$, (d) compounds of the formula

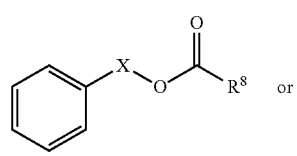

(d)

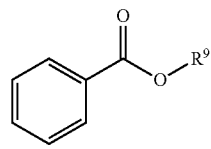

(d')

wherein $R^8$ is methyl, $C_3$-$C_4$ alkyl, $C_3$-$C_4$ alkenyl, —$(CH_2)_2$-Ph, or —CH=CH-Ph;

X is —CH=CH—$CH_2$— or —$(CH_2)_n$—, wherein n is 1 or 2; and $R^9$ is isobutyl or phenylethyl;

(e) compounds of the formula

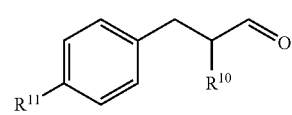

(e)

wherein
R¹⁰ is hydrogen or methyl; and
R¹¹ is a C₃-C₄ alkyl, e.g. isopropyl, isobutyl or tert-butyl,
and
(f) 2-heptylcyclopentanone, 2-ethoxynaphthalene, 2-methoxynaphthalene, 1-methoxy-4-(prop-1-enyl)benzene and 1-(cyclopropylmethyl)-4-methoxybenzene.

Particularly preferred is the use of compounds selected from the list consisting of 2-cyclohexylidene-2-phenylacetonitrile, 2-cyclopentylidene-2-phenylacetonitrile, 3-ethyl-2-phenylpent-2-enenitrile, 2-ethoxy-4-(isopropoxymethyl)phenol, 2-ethoxy-4-(methoxymethyl)phenol, phenethyl cinnamate, 4-allyl-2-methoxyphenyl 2-phenylacetate, n-hexyl salicylate, cis-3-hexen-1-yl salicylate, cyclohexylsalicylate (=cyclohexyl 2-hydroxybenzoate), amylsalicylate (=pentyl 2-hydroxybenzoate), isobutylsalicylate (=isobutyl 2-hydroxybenzoate), phenylethyl benzoate, benzyl 2-methylbut-2-enoate, 2-methyl-3-(4-isopropylphenyl)propanal, isobutyl benzoate, cinnamyl cinnamate, phenethyl salicylate, 2-methyl-3-(4-(2-methylpropyl)phenyl)propanal, 2-heptylcyclopentanone, 2-ethoxynaphthalene, 2-methoxynaphthalene, 1-methoxy-4-(prop-1-enyl)benzene, phenethyl pivalate, 1-(cyclopropylmethyl)-4-methoxybenzene, cinnamyl acetate, 3-(4-tert-butylphenyl)propanal, phenethyl 2-methylbutanoate, and phenethyl isobutyrate.

The availability of a greater number of compounds, which in addition to their odoriferous properties, have the ability to reduce or suppress the formation of skin irritation provides the perfumer with an adequate amount of molecules some of which posses quite varied odor notes, to create hedonically attractive fragrance compositions while providing reduction of skin irritation and/or redness reduction activity to the skin to which it is applied. In particular, the use of multiple perfume ingredients permits the design of hedonically attractive fragrance accords.

The actives for reducing skin irritation as hereinabove described may be combined with all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art. Such ingredients are, for example, described in "Perfume and Flavor Materials of Natural Origin", S. Arctander, Ed., Elizabeth, N.J., 1960; "Perfume and Flavor Chemicals", S. Arctander, Ed., Vol. I & II, Allured Publishing Corporation, Carol Stream, USA, 1994; and "International cosmetic ingredient dictionary" 6th ed., The Cosmetic, Toiletry and Fragrance Association, Inc., Washington, 1995.

While lower concentrations of the active compound show an effect in a cell culture system, as can be seen from the examples, higher concentrations in personal care products are necessary to allow for an effective concentration on the human skin even if, for example part of the product may be removed by abrasion of clothes or may be diluted by sweat. Furthermore, the healthy skin acts as a barrier which limits the penetration of the active compounds. Generally, the concentration of active compound needed for efficaciousness on skin is from about 50 to 100 times higher than that needed in in-vitro tests. The usual perfume concentration in a topical cosmetic product is about 0.3 to 2% by weight. In general, the amount of actives applied is in the range of from 0.2 to 2% by weight, based on the end-product applied to the skin, the amounts applied usually being in the range of from 0.3 to 1% by weight.

Thus the present invention refers in a further aspect to fragrance compositions comprising at least 30 weight % based on the total fragrance composition of at least two actives for reducing skin irritation as hereinabove described.

Whereas some active compounds may be used in relatively high amounts in a fragrance composition others which are known to be very powerful odorants, such as Neroline™ and Propyl Diantilis, may be used only in smaller amounts in order to avoid negatively effecting the overall hedonic impression of the fragrance composition. In general, as the overall proportion of the active compound in the fragrance composition rises, so should the number of active compounds used. For example, a fragrance composition comprising more than 40 weight % of active compounds should preferably contain at least 4 different actives, a fragrance composition comprising more than 50 weight % of active compounds should preferably contain at least 5 different actives, and a fragrance compositions comprising more than 60 weight % of active compounds should preferably contain at least 6 different actives. Thus, in a further aspect the present invention refers to fragrance compositions comprising at least 30 weight % of at least three, four or five actives for reducing skin irritation. Optionally the fragrance composition according to the present invention comprises at least two, three or four actives of which are selected from a different group of compounds, namely group (a), (b), (c), (d), (e), and (f) as hereinabove described.

From a hedonic point of view the actives are selected from two different group of compounds. In particular embodiments are fragrance compositions comprising a compound of formula (a) and a compound of formula (b), and fragrance compositions comprising a compound of formula (c) and a compound of formula (d) or (d'). As can be seen from the examples, fragrance compositions which are both hedonically attractive and which have irritation reducing properties may be prepared, for example, if the composition comprises at least four active compounds, each of which is selected from a different group of compounds.

In an other embodiment the invention is directed to fragrance compositions comprising (a) at least one compound of the formula

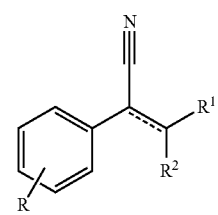

(a)

wherein
R is hydrogen or isopropyl;
R¹ is methyl or ethyl; and R² is C₁-C₆ alkyl or C₂-C₆ alkenyl; or
R¹ and R² together with the carbon atom to which they are attached form a C₅ or
C₆ cycloalkyl ring; and
the dotted line together with the carbon carbon bond represents a single bond or a double bond;

(b) at least one compound of the formula

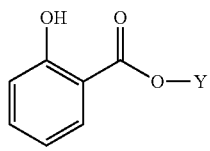

wherein Y is a $C_4$-$C_7$ hydrocarbon residue, e.g. cyclohexyl, n-hexyl, n-pentyl, iso-butyl, cis-3-hexen-1-yl, phenethyl, and 1-methyl-hex-3-en-1-yl;

(c) at least one compound of the formula

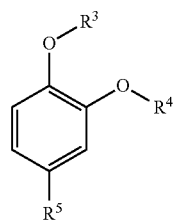

wherein
$R^4$ is methyl or ethyl and
I) $R^3$ is hydrogen and $R^5$ is —$CH_2$—O—$R^6$, wherein $R^6$ is methyl or isopropyl; or
II) $R^3$ is —C(O)—$R^7$, wherein $R^7$ is benzyl, and $R^5$ is —$CH_2$—CH=$CH_2$; and (d) at least one compound of the formula

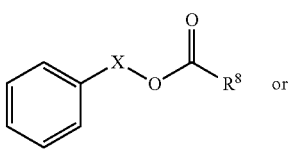

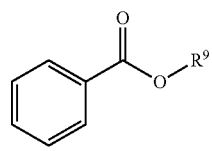

wherein
$R^8$ is methyl, $C_3$-$C_4$ alkyl, $C_3$-$C_4$ alkenyl, —$(CH_2)_2$-Ph, or —CH=CH-Ph;
X is —CH=CH—$CH_2$— or —$(CH_2)_n$—, wherein n is 1 or 2; and
$R^9$ is isobutyl or phenylethyl.

Furthermore, the present invention refers to topical skin care compositions, such as cosmetic products and personal wash products, comprising about 0.2 to about 3 weight %, preferably about 0.5 to about 2.5 weight % of a fragrance composition, the fragrance composition containing at least 30 weight % of at least two actives selected from the group (a), (b), (c), (d), (e), and (f) as hereinabove described, with the proviso that the topical skin care composition comprises at least 0.2 weight % of actives based on the total amount of the skin composition. In particular embodiments are topical skin care compositions wherein the fragrance composition containing a compound of formula (a) and a compound of formula (b), and topical skin care composition wherein the fragrance composition containing a compound of formula (c) and a compound of formula (d) or (d').

In another aspect the present invention is directed to a method of reducing the onset of skin irritation by applying to the skin an effective amount of a topical skin care composition comprising a fragrance composition, the fragrance composition containing at least 30 weight % based on the total fragrance composition of at least two actives as defined hereinabove, with the proviso that the topical skin care composition comprises at least 0.2 weight % of actives based on the total amount of the skin composition.

An "effective amount" is generally achieved if about 5-50 $mg/cm^2$ skin or about 0.05 to about 0.5 mm thick film of the topical skin product is applied to the skin.

As used within the meaning of the present invention the expression "at least 30 weight %" includes fragrance compositions comprising at least 35, 40 or even 45 or 50 weight % of at least two actives as defined hereinabove. The term "actives" and "active compounds" as used within the meaning of the present invention refers to all compounds selected from the list of compounds of formula (a), (b), (c), (d), (d'), (e) and 2-heptylcyclopentanone, 2-ethoxynaphthalene, 2-methoxynaphthalene, 1-methoxy-4-(prop-1-enyl)benzene and 1-(cyclopropylmethyl)-4-methoxybenzene.

Topical skin care compositions of the present invention may be divided into two classes of products, that is, cosmetic products and topical washing products, and may include but is not limited to antiperspirants, deodorants, day and night creams, shaving products, hand creams, body lotions, hair shampoo and conditioners, lipsticks, after-sun products, hand lotions, foundation creams, moisturizing creams, skin food, skin tonics, skin lightening products and overnight facial masks. The compositions may be in any form. These forms may include lotions, creams, sticks, roll-on formulations, mousses, aerosol sprays, pad-applied formulations, powders, tonics, and emulsions (oil-in-water, water-in-oil, or mixed emulsion systems).

The invention is now further described with reference to the following non-limiting examples. All of the amounts are given as percentage amounts by weight, unless otherwise indicated.

EXAMPLE 1

Screening for Compounds Protecting Keratinocytes Against Irritating Agents

Normal human epidermal keratinocytes (NHEK) were obtained from skin biopsies and maintained as described by Rheinwald and Green (cell, 6:331-344, 1975) in keratinocyte growth medium supplemented with 10% heat inactivated fetal calf serum at a humidity of 98% in a 5% carbon dioxide atmosphere. A confluent culture was trypsinated and adjusted to a density of $5 \times 10^4$ cells/ml. The cells were then seeded in the same medium but with only 1% fetal calf serum in 24 well plates and cultivated for a period of 48 h. A model irritating agent was then applied to the cells by adding calcimycin to a final level of 2.5 μM. The individual compounds, as listed below, dissolved in DMSO were added simultaneously. The final concentration of the compounds was 50 μM or 10 μM, the final DMSO concentration was adjusted to 1% (v/v). Parallel treatments received no calcimycin (non-irritated control) or calcimycin without compounds according to the present invention (irritated control). The DMSO concentration was adjusted to 1% in all these control treatments. After 24 h incubation, the supernatant of the cells was harvested, diluted 1:1 and added to an enzyme linked immunoassay kit for the specific detection of prostaglandin $E_2$ as a marker of cellular irritation (Product #404110, Neogen corporation, Lexington Ky. 40505, USA). The prostaglandin levels in treated cell cultures were compared to the irritated and non-irritated control cultures in order to determine the relative inhibition of $PGE_2$ formation. Results for the individual compounds are listed below.

| Compound | relative inhibition in % of $PGE_2$ formation in keratinocyte cultures at | |
|---|---|---|
| | 50 μM | μM |
| PEONILE ® (2-cyclohexylidene-2-phenylacetonitrile) | 93.3 | 92.4 |
| PROPYL DIANTILIS (2-Ethoxy-4-(isopropoxymethyl)phenol) | 90.9 | 95.1 |
| METHYL DIANTILIS ® (2-Ethoxy-4-(methoxymethyl)phenol) | n.d. | 88.2 |
| Phenethyl cinnamate | 91.7 | 93.6 |
| EUGENYL PHENYL ACETATE (Phenyl 2-(4-allyl-2-methoxyphenyl)acetate) | 96.6 | 99 |
| n-Hexyl salicylate | 82.9 | 91.6 |
| cis-3-Hexen-1-yl salicylate | 94.8 | 81.4 |
| Cyclohexyl salicylate | 97.4 | 76.6 |
| Amyl salicylate | 89.8 | 73.5 |
| Isobutyl salicylate | 69.1 | 73.1 |
| Phenethyl benzoate | 92.4 | 56.9 |
| TIGLATE BENZYLE (benzyl 2-methylbut-2-enoate) | 72.4 | 50.2 |
| CYCLAMEN ALDEHYDE ™ (2-Methyl-3-(4-isopropylphenyl)propanal) | 82.0 | 32 |
| Isobutyl benzoate | 52.5 | n.d. |
| Cinnamyl cinnamate | 64.0 | n.d. |
| Phenethyl salicylate | 50.9 | n.d. |
| SILVIAL ® (2-Methyl-3-(4-(2-methylpropyl)phenyl)propanal) | 62.7 | n.d. |
| ALISMONE ™ (2-heptylcyclopentanone) | 92.4 | 47 |
| NEROLINE ™ CRIST (2-ethoxynaphthalene) | 83 | 50.2 |
| YARA YARA ™ (2-methoxynaphthalene) | 78 | 46 |
| ANETHOLE (1-methoxy-4-(prop-1-enyl)benzene) | 51 | n.d. |
| CENTIFOLYL ™ (phenethyl pivalate) | 39 | n.d. |
| TOSCANOL ® (1-(cyclopropylmethyl)-4-methoxybenzene) | 56.7 | n.d. |
| Cinnamyl acetate | 47.8 | n.d. |
| BOURGEONAL ™ (3-(4-tert-butylphenyl)propanal) | 65.0 | n.d. |
| ANATOLYL ™ (phenethyl 2-methylbutanoate) | 50.5 | n.d. |
| Phenethyl isobutyrate | 44.8 | n.d. |
| 2-Cyclopentylidene-2-phenylacetonitrile | 80.8 | 71.1 |
| 3-Ethyl-2-phenylpent-2-enenitrile | 73.2 | 63.9 | n.d. = not determined

Similar results as listed above were obtained by irritation of the cells either by UVB irradiation or exposure to the skin cells to irritating cationic surfactant benzalkonium chloride.

EXAMPLE 2

Fragrance Compositions with the Properties to Reduce or Suppress the Formation of Skin Irritation 2.1 Floral Fragrance Composition No. 1

| | parts by weight 1/100 |
|---|---|
| Peonile ® | 18.90 |
| Alismone ™ | 5.30 |
| Cyclohexyl salicylate | 12.10 |
| Silvial ® | 6.80 |
| Toscanol ® | 0.15 |
| Floral fragrance base | 56.75 |

2.2 Floral Fragrance Composition No. 2

| | parts by weight 1/100 |
|---|---|
| PEONILE ® | 1.00 |
| PROPYL DIANTILIS | 0.01 |
| Phenethyl cinnamate | 0.20 |
| Hexyl salicylate | 40.00 |
| cis-3-Hexen-1-yl salicylate | 1.00 |
| Amyl salicylate | 3.00 |
| NEROLINE ™ | 0.10 |
| Floral fragrance base | 54.69 |

2.3 Floral-Fruity Fragrance Composition No. 3

| | parts by weight 1/900 |
|---|---|
| Citronellyl acetate | 10 |
| Cyclamen aldehyde ™* | 3 |
| Ambrettolide (oxacycloheptadec-10-en-2-one) | 40 |
| Ambrofix (CAS No. 6790-58-5) 10% in dipropyleneglycol | 8 |
| Bourgeonal ™* | 30 |
| Centifolyl ™* | 45 |
| Dihydromyrcenol (2,6-dimethyloct-7-en-2-ol) | 8 |
| Ethyllinalool (3,7-dimethyl-1,6-nonadien-3-ol) | 45 |
| Florol ® (tetrahydro-2-isobutyl-4-methyl-2H-pyran-4-ol) | 25 |
| Galaxolide ® (1,3,4,6,7,8-hexahydro-4,6,6,7,8,8-hexamethyl-cyclopenta-gamma-2-benzopyran) 50% dissolved in isopropylmyristate | 12 |
| Hedione ® (methyl 2-(3-oxo-2-pentylcyclopentyl)acetate) | 250 |
| Cis-3-hexenol 10% in dipropyleneglycol | 3 |
| Phenethyl isobutyrate* | 25 |
| Ethyl-2-methyl-butyrate 10% in dipropyleneglycol | 3 |
| Neroline ™* 10% in dipropyleneglycol | 2 |
| Orange essence brazil | 15 |
| Pomarose (5,6,7-trimethylocta-2,5-dien-4-one) 10% in dipropyleneglycol | 3 |
| Prunella ® subst (compounded perfumery base from Firmenich) | 3 |
| Cyclohexyl salicylate* | 75 |
| cis-3-Hexen-1-yl salicylate* | 100 |
| n-Hexyl salicylate* | 20 |
| Phenylethyl salicylate* | 80 |
| Silvial ®* | 45 |
| Tropional (2-methyl-3-(3,4-methylenedioxyphenyl)-propanal) | 40 |
| Velvione ® (5-cyclohexadecen-1-one) | 10 |

All ingredients marked with an * are active compounds having the ability to reduce or suppress the formation of skin irritation, as defined according to the present invention. The fragrance composition No. 3 comprises 47 weight % of actives.

2.4 Floral-Fruity Fragrance Composition No. 4

| | parts by weight 1/900 |
|---|---|
| Benzyl-acetate | 14 |
| 2-Phenylethanol | 200 |
| Cyclamen aldehyde ™* | 3 |
| Bourgeonal ™* | 3 |
| Centifolyl ™* | 80 |
| Phenethyl-cinnamate* | 25 |
| Citronellol | 25 |
| 1-(1,1-Dimethoxypropan-2-yl)benzene | 8 |

-continued

| | parts by weight 1/900 |
|---|---|
| Dione (2-[2-(3,3,5-trimethylcyclohexyl)-1-ethanone]cyclopentanone) 10% in dipropyleneglycol | 3 |
| Dipropyleneglycol | 128 |
| Gardenol (alpha-Methylbenzyl acetate) | 5 |
| Georgywood (1-(1,2,3,4,5,6,7,8-octahydro-1,1,7,8-tetramethyl-naphthalen-7-yl)ethanone) | 2 |
| Geraniol | 30 |
| Hedione ® | 70 |
| Heliotropine | 4 |
| Indolene (8-(1H-indol-2-yl)-8-(1H-indol-3-yl)-2,6-dimethyloctan-2-ol) | 1 |
| Isoraldeine 70 (mixture of 4/1-(2,6,6-trimethyl-2-cyclohexen-1-yl)-3-methyl-3-buten-2-one) | 25 |
| Methyl diantilis ®* | 25 |
| Neroline ™* | 1 |
| Patchouli essential oil rectified (origin: Indonesia) | 2 |
| Peach pure (5-heptyl-dihydrofuran-2(3H)-one) | 10 |
| Pharaone (2-Cyclohexyl-1,6-heptadien-3-one) 1% in dipropyleneglycol | 8 |
| Pomarose 10% in dipropyleneglycol | 3 |
| Rose oxide | 7 |
| Cyclohexyl salicylate* | 45 |
| cis-3-Hexenyl salicylate* | 55 |
| n-Hexyl salicylate* | 20 |
| Phenethyl salicylate* | 80 |
| Vanillin | 5 |
| Viridine (phenylacetaldehyde dimethyl acetal) | 3 |
| Ylang Ylang essential oil | 10 |

All ingredients marked with an * are active compounds having the ability to reduce or suppress the formation of skin irritation, as defined according to the present invention. The fragrance composition No. 3 comprises 37.4 weight % of actives.

2.5 Fresh, Woody Floral Fragrance Composition No. 5

| | parts by weight 1/1000 |
|---|---|
| Azurone 10% in triethyl citrate (7-(3-Methylbutyl)-2H-1,5-benzodioxepin-3(4H)-one) | 4 |
| Ethyl vanilline 10% in DPG | 4 |
| Evernyl ™ (methyl 2,4-dihydroxy-3,6-dimethylbenzoate) | 2 |
| Fixolide (1-(3,5,5,6,8,8-hexamethyl-5,6,7,8-tetrahydronaphthalen-2-yl)ethanone) | 55 |
| Florhydral ® (3-(3-isopropylphenyl)butanal) | 5 |
| Iso E super ™ (1-(2,3,8,8-tetramethyl-1,2,3,4,5,6,7,8-octahydro-naphthalen-2-yl)ethanone) | 250 |
| Kephalis (4-(1-ethoxyvinyl)-3,3,5,5-tetramethylcyclohexanone) | 30 |
| Cyclohexal | 80 |
| Linalool (3,7-dimethylocta-1,6-dien-3-ol) | 40 |
| Patchouli essential oil | 10 |
| Peonil ®* | 100 |
| Diethyl phthalate | 60 |
| Radjanol ™ (2-ethyl-4-(2,2,3-trimethyl-3-cyclopenten-1-yl)-2-buten-1-ol) | 50 |
| Phenethyl salicylate* | 100 |
| cis-3-Hexen-1-yl salicylate* | 55 |
| n-Hexyl salicylate* | 55 |
| Serenolide ™ (2-(1-(3,3-dimethylcyclohexyl)ethoxy)-2-methylpropyl cyclopropanecarboxylate) | 60 |
| Velvione ® | 40 |

All ingredients marked with an * are active compounds having the ability to reduce or suppress the formation of skin irritation, as defined according to the present invention. The fragrance composition No. 5 comprises 31 weight % of actives.

2.6 Floral, Spicy, Green Fragrance Composition No. 6

| | parts by weight 1/948 |
|---|---|
| Dimethyl benzyl carbinyl acetate | 25 |
| Linalyle acetate | 70 |
| Phenylethyl alcohol | 75 |
| Methyl anthranilate | 3 |
| Cosmone (3-methylcyclotetradec-5-enone) | 40 |
| Florol ® (2-isobutyl-4-methyltetrahydro-2H-pyran-4-ol) | 70 |
| Galbanum oil | 35 |
| Gardenol | 15 |
| Hedione ® | 55 |
| Indole 1% in dipropyleneglycol (DPG) | 45 |
| Isoraldeine 70 | 80 |
| Methyl diantilis ®* | 45 |
| Nirvanolide ™ (13-methyloxacyclopentadec-10-en-2-one) | 45 |
| Peche pure | 3 |
| Peonile ®* | 55 |
| EUGENYL PHENYL ACETATE* | 20 |
| Phenethyl salicylate* | 100 |
| Cis-3-Hexen-1-yl salicylate* | 100 |
| Vertofix coeur (methyl cedryl ketone) | 55 |
| Ylang Ylang essential oil | 12 |

All ingredients marked with an * are active compounds having the ability to reduce or suppress the formation of skin irritation, as defined according to the present invention. The fragrance composition No. 6 comprises 33.7 weight % of actives.

2.7 Floral, Rosy, Fruity Fragrance Composition No. 7

| | parts by weight 1/825 |
|---|---|
| Benzyl-acetate | 20 |
| 2-Phenylethanol | 200 |
| Phenethyl benzoate* | 130 |
| Centifolyl ®* | 45 |
| Cinnamyl cinnamate* | 10 |
| Phenyl ethyl cinnamate* | 52 |
| Citronellol | 45 |
| Dihydrofarnesal ™ (3,7,11-trimethyldodeca-6,10-dienal) | 20 |
| Florhydral ™ (3-(3-isopropylphenyl)butanal) | 3 |
| Hedione ® | 150 |
| Phenethyl isobutyrate* | 25 |
| Isoraldeine 70 | 45 |
| Methyl diantilis ®* | 45 |
| Peche pure | 10 |
| Rose oxide | 10 |
| Vanillin | 15 |

All ingredients marked with an * are active compounds having the ability to reduce or suppress the formation of skin irritation, as defined according to the present invention. The fragrance composition No. 7 comprises 37.2 weight % of actives.

EXAMPLE 3

Effect of Fragrance Compositions on Keratinocyte Cultures

Keratinocytes were grown in 24 well plates and irritated with calcimycin as described in example 1. Fragrance compositions of example 2 were dissolved in DMSO and added to the cultures simultaneously. Inhibition of $PGE_2$ formation was measured as described in example 1. The results are listed in Table 1.

TABLE 1

| | Relative inhibition in % of PGE$_2$ formation at different concentration of test fragrance | |
|---|---|---|
| | 12.5 ppm | 6.25 ppm |
| Composition No. 1 | 79.0 | 42.4 |
| Composition No. 2 | 82.6 | 85.6 |
| Floral fragrance base | 0 | 0 |

As can been seen from the figures in Table 1, about 80% reduction of PGE$_2$ formation was observed at 12.5 ppm if a fragrance composition according to the present invention is applied, whereas using the floral fragrance base without actives, no measurable reduction of PGE$_2$ formation was observed.

EXAMPLE 4

Irritation Reducing Effects of a Hydrogel on Reconstituted Epidermis

A hydrogel was prepared as follows:

| INGREDIENT | SUPPLIER | INCI NAME | % W/W |
|---|---|---|---|
| CARBOPOL 980 | Goodrich | Carbomer | 0.50 |
| PEMULEN TR1 | Goodrich | Acrylate/C10-C30 Alkyl acrylate crosscopolymer | 0.20 |
| LUBRAGEL CG | Guardian | Polyglycerylmethacrylate & Propylene glycol | 0.50 |
| UCON 75H450 | Amerchol | PEG/PPG-17/6 copolymer | 1.00 |
| GLYCERIN | AMI | Glycerin | 4.00 |
| HEXYLENE GLYCOL | | Hexylene Glycol | 2.00 |
| DEIONISED WATER | | Water | qsq 100.00 |
| GERMALL 115 | Sutton | Imidazolidinyl Urea | 0.60 |
| SODIUM HYDROXIDE 10% in water | | Sodium Hydroxide | qsp pH = 5.50 |
| CREMOPHOR RH 40 | BASF | PEG 40 Hydrogenated Castor oil | 1.00 |

Glycerin and water were mixed, Carbopol 980 was dispersed, then Pemulen TR 1 and then the remaining ingredients were added.

Human reconstituted epidermis EpiDerm was purchased from Mattek (Ashland, USA). The cultures were exposed to a single Dose of 600 mJ UVB, and then either 50 mg phosphate buffered saline (PBS) or 50 mg of the above hydrogel was added on top of the individual EpiDerm cultures. After 24 h incubation, the culture medium beneath the air exposed EpiDerm cultures was sampled and analyzed for PGE$_2$ as described in example 1. All skin samples retained 100% cellular viability throughout the experiment. Skin samples treated with a hydrogel containing the inventive perfume composition 1 from example 2 suppressed UVB induced PGE$_2$ formation.

TABLE 2

| | level PGE$_2$ per ml culture medium | t-test vs control | t-test vs UVB irritation |
|---|---|---|---|
| Control, no UVB | 8.253 | 1.000 | |
| UVB 600 mJ, PBS treatment | 42.143 | 0.003 | 1.000 |
| UVB 600 mJ, Hydrogel treatment | 48.778 | 0.046 | 0.742 |
| UVB 600 mJ, Hydrogel containing 0.5% (w/w) fragrance comp. No. 1 | 12.135 | 0.384 | 0.001 |

EXAMPLE 5

Antiperspirant with Reduced Irritation on Reconstituted Epidermis

An antiperspirant was formulated according the following formulation:

| | Weight % |
|---|---|
| Water | 67 |
| Aluminium chlorohydrate | 20 |
| Glycerin | 5 |
| Sunflower oil | 4 |
| Steareth 2 | 3 |
| Steareth-20 | 1 |

The following antiperspirant compositions had been prepared:
I) antiperspirant & 1 weight % conventional perfume A
II) antiperspirant & 0.5 weight % conventional perfume B
III) antiperspirant & 0.5 weight % fragrance composition No. 1 (Ex. 2.1)
IV) antiperspirant & 1 weight % fragrance composition No. 1 (Ex. 2.1)

50 mg of the resulting antiperspirant I)-IV) or 50 mg of PBS as control was added to Mattek skin cultures as described above, and after 24 h the level of PGE$_2$ in the culture medium was determined according to the procedure described above. The results are shown in Table 3.

TABLE 3

| | Level of PGE$_2$ in culture medium | t-test vs control |
|---|---|---|
| PBS | 12.54 | |
| Composition I) | 35.49 | 0.002 |

TABLE 3-continued

| | Level of PGE$_2$ in culture medium | t-test vs control |
|---|---|---|
| Composition II) | 27.66 | 0.011 |
| Composition III) | 16.05 | 0.302 |
| Composition IV) | 9.48 | 0.368 |

As can be seen from the results above, antiperspirants formulated with conventional perfumes (i.e. composition I) and II)) led to significantly enhanced PGE$_2$ formation indicating an irritating nature of these products to the human skin, whereas upon treatment of EpiDerm with antiperspirants containing the inventive fragrance composition, no significantly enhanced PGE$_2$ levels were detected. All epidermal cultures retained 100% of the cellular viability showing that all the products are not cytotoxic.

The invention claimed is:

1. A method of reducing the onset of skin irritation caused by either environmental stresses or by stresses caused by the application of chemical compounds to skin, by applying to the skin an effective amount of a topical skin care composition comprising both:
at least one (a) compound of the following formula

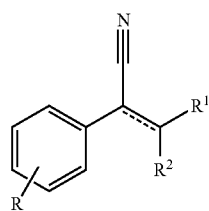

(a)

wherein
R is hydrogen or isopropyl;
R$^1$ is methyl or ethyl; and R$^2$ is C$_1$-C$_6$ alkyl or C$_2$-C$_6$ alkenyl; or
R$^1$ and R$^2$ together with the carbon atom to which they are attached form a C$_5$ or C$_6$ cycloalkyl ring; and
the dotted line together with the carbon carbon bond represents a single bond or a double bond;
and,
at least one (b) compound of the following formula

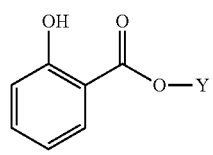

(b)

wherein Y is a C$_4$-C$_7$ hydrocarbon residue, wherein the total amount of both compound (a) and compound (b) is at least 0.2% wt. of the total amount of the topical skin care composition.

2. A method of reducing the onset of skin irritation caused by either environmental stresses or by stresses caused by the application of chemical compounds to skin, comprising the steps of:
(A) providing a topical skin care composition which includes a fragrance composition comprising both:
at least one (a) compound of the following formula

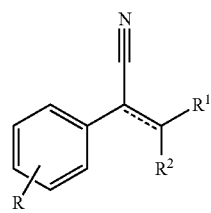

(a)

wherein
R is hydrogen or isopropyl;
R$^1$ is methyl or ethyl; and R$^2$ is C$_1$-C$_6$ alkyl or C$_2$-C$_6$ alkenyl; or
R$^1$ and R$^2$ together with the carbon atom to which they are attached form a C$_5$ or C$_6$ cycloalkyl ring; and
the dotted line together with the carbon carbon bond represents a single bond or a double bond;
and,
at least (b) one compound of the following formula

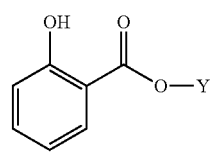

(b)

wherein Y is a C$_4$-C$_7$ hydrocarbon residue,
wherein the total amount of both compound (a) and compound (b) is at least 30% of the total weight of the fragrance composition present in the topical skin care composition; and,
(B) topically applying to the skin an amount of the topical skin composition which is effective for reducing skin irritation.

3. A method of reducing the formation of prostaglandins in skin cells by applying to the skin cells an effective amount of a topical skin care composition comprising a fragrance composition containing both:
at least one (a) compound of the following formula

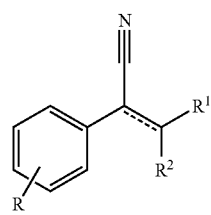

(a)

wherein
R is hydrogen or isopropyl;
R$^1$ is methyl or ethyl; and R$^2$ is C$_1$-C$_6$ alkyl or C$_2$-C$_6$ alkenyl; or
R$^1$ and R$^2$ together with the carbon atom to which they are attached form a C$_5$ or C$_6$ cycloalkyl ring; and
the dotted line together with the carbon carbon bond represents a single bond or a double bond; and, at least one (b) compound of the following formula

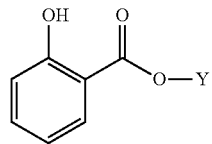

wherein Y is a $C_4$-$C_7$ hydrocarbon residue wherein the total amount of both compound (a) and compound (b) is at least 0.2% wt. of the total amount of the topical skin care composition.

4. A method of reducing the formation of prostaglandins in skin cells by applying to the skin cells an effective amount of a topical skin care composition comprising a fragrance composition containing both:

at least one (a) compound of the following formula

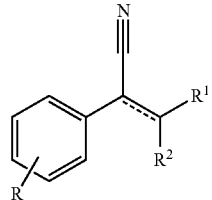

wherein
R is hydrogen or isopropyl;
$R^1$ is methyl or ethyl; and $R^2$ is $C_1$-$C_6$ alkyl or $C_2$-$C_6$ alkenyl; or
$R^1$ and $R^2$ together with the carbon atom to which they are attached form a $C_5$ or $C_6$ cycloalkyl ring; and
the dotted line together with the carbon carbon bond represents a single bond or a double bond; and,
at least one (b) compound of the following formula

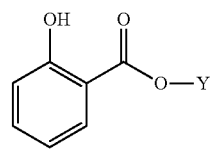

wherein Y is a $C_4$-$C_7$ hydrocarbon residue wherein the total amount of both compound (a) and compound (b) is at least 30% wt. of the total amount of the fragrance composition present in the topical skin care composition.

* * * * *